United States Patent [19]

Stark et al.

[11] Patent Number: 4,522,594
[45] Date of Patent: Jun. 11, 1985

[54] LIGHT SHIELD FOR A DENTAL HANDPIECE

[75] Inventors: Marvin M. Stark, Los Altos Hills; Kenneth B. Soelberg, Menlo Park; Roger B. Pelzner, San Mateo, all of Calif.

[73] Assignee: Marvin M. Stark Research Foundation, San Jose, Calif.

[21] Appl. No.: 459,818

[22] Filed: Jan. 21, 1983

[51] Int. Cl.³ .............................................. A61C 3/00
[52] U.S. Cl. ....................................... 433/141; 433/229
[58] Field of Search ................... 433/32, 82, 229, 141; 128/633, 22, 68.1, 82.1, 802

[56] References Cited

U.S. PATENT DOCUMENTS

| 881,469 | 3/1908 | Hale | 433/81 |
| 3,018,778 | 1/1962 | Brilliant | 433/141 |

FOREIGN PATENT DOCUMENTS

| 2846471 | 5/1980 | Fed. Rep. of Germany | 433/141 |
| 280578 | 10/1928 | United Kingdom | 128/22 |

Primary Examiner—Gene Mancene
Assistant Examiner—John G. Weiss
Attorney, Agent, or Firm—Lothrop & West

[57] ABSTRACT

A dental handpiece especially for transmitting intense light for use in polymerizing dental materials in situ has a readily removable opaque shield of deformable material affixed to the end thereof to preclude the light from spreading and to prevent inadvertent contact of the handpiece tip with the subjacent area.

1 Claim, 3 Drawing Figures

LIGHT SHIELD FOR A DENTAL HANDPIECE

BRIEF SUMMARY OF THE INVENTION

A dental handpiece especially for conducting intense light to a site of polymerization of tooth restorative material has a removable shield for confining the light to a selected area, for preventing the general dissemination of the light, and for preventing contact of the handpiece with the material being polymerized and adjacent teeth.

PRIOR ART

The applicants are not aware of pertinent prior art.

DETAILED DESCRIPTION

Figure 1:
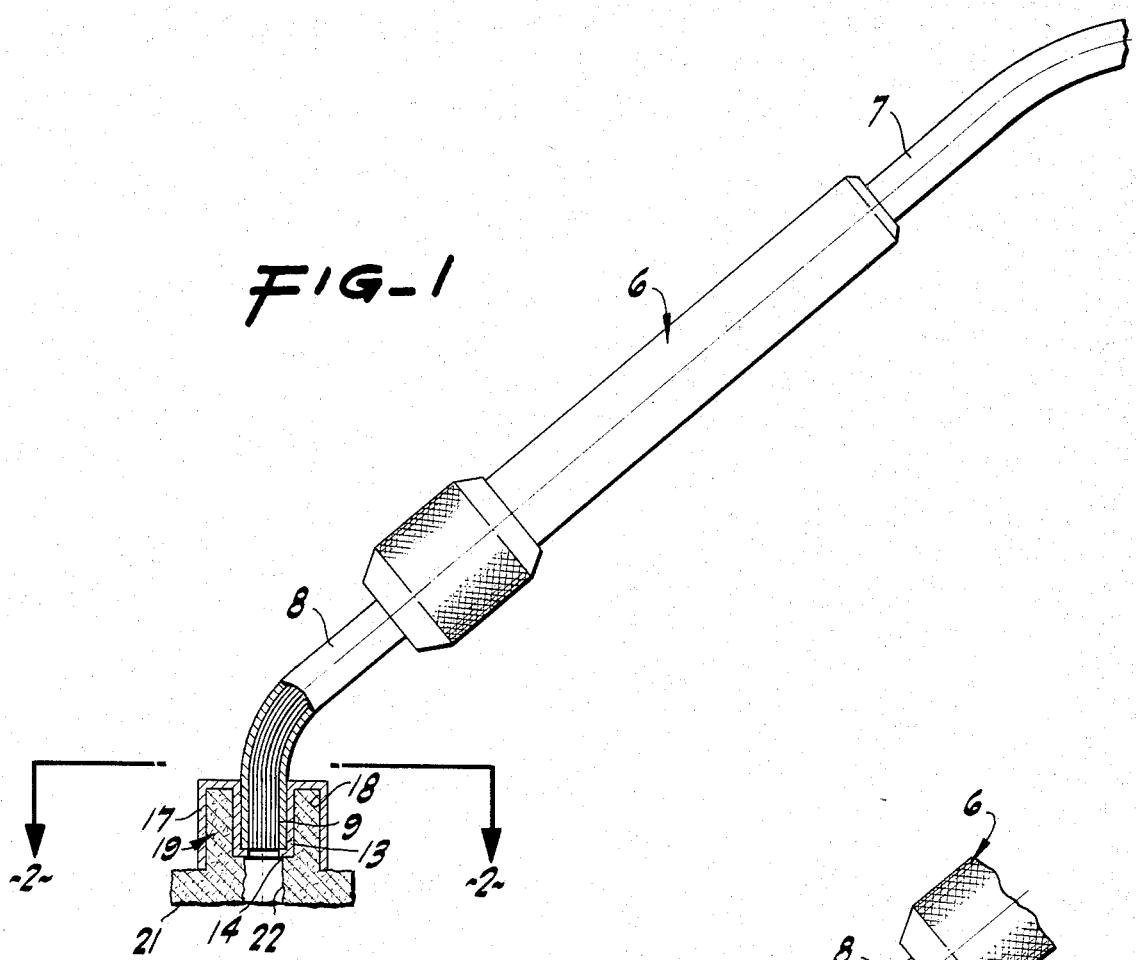
FIG. 1 is a side elevation of a dental handpiece with one end portion broken away and the other portion broken partly away to show the interior construction in cross-section on a transverse axial plane.
Figure 3:
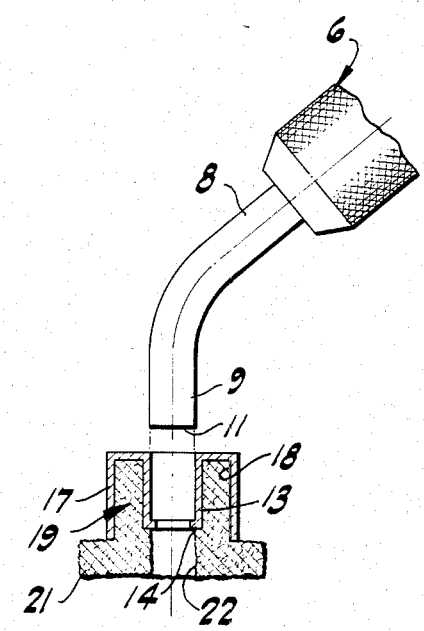
FIG. 3 is a cross-section, similar to a portion of FIG. 1, but with some parts disassembled.
Figure 2:
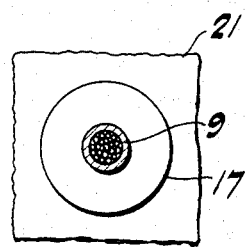
FIG. 2 is a cross-section, the plane of which is indicated by the line 2—2 of FIG. 1.

Currently it is the practice in dentistry to utilize for tooth restoration and comparable work relatively modern materials very effective for their purpose but which require curing in situ by appropriate illumination thereof from an intense light source and for a substantial time. While all of this technique is well understood, there is a side effect, particularly for the dentist, in that the intense light utilized over a protracted time on each patient and many times during the day may very well cause optical difficulties especially for the dentist and also for an attending nurse or other bystanders.

In accordance with the invention, therefore, we have provided a means to mitigate the difficulty and having other advantages.

In the customary instance there is afforded a dental handpiece 6 of any convenient size and shape, usually rectilinear for the most part and having a connection 7 to an appropriate light source (not shown). This source is ordinarily of high intensity and transmits very intense light to the handpiece 6 and through the handpiece by means of a fiber optic bundle or the like. The handpiece 6 includes an extension 8 having a curvilinear configuration ending in a circular cylindrical tip 9 with a squared-off end 11.

In the usual practice, the handpiece is brought into position with the tip 9 close to the subjacent surface of the tooth or material to be treated or polymerized. Under most circumstances, a great deal of the light is scattered or escapes to the general surroundings.

In the present case, there is fitted over the tip 9 a shield structure inclusive of a circular cylindrical collar 13. This is frictionally engageable with the generally cylindrical end of the tip and has an inturned, end flange 14 disposed so as to abut against the end of the tip when the shield is fully in place. The flange is short enough to leave a central opening. An annular wall connects the collar 13 with an outer sleeve 17. This is of circular cylindrical configuration and extends axially somewhat beyond the end of the wall 14.

The collar 13 and the wall 17 define an annular space 18 into which is fitted the correspondingly annular portion of a shield 19 of yieldable, spongy or flexible material. The shield configuration is inclusive of an extensive flange 21 preferably rectangular in end outline and inclusive of a central, unobstructed or clear passage 22. The annular portion of the deformable shield 19 can readily be inserted into the annular space in the tip. There is some deformation to afford sufficient frictional engagement between the shield 19 and walls 13 and 17 as readily to be held in place during all ordinary maneuvers. Yet, the shield 19 can manually be readily removed for changing or can be left permanently in position in the collor and can be removed with the collar from the tip. The material of the shield 19 (as well as that of the sleeve 17) is relatively opaque.

For use, the dentist brings the handpiece 6 into the position desired and abuts or contacts the shield 19 against the surface of the tooth or teeth adjacent to or overlying the area where the material for polymerization is disposed. He then energizes the light source and shines light onto the polymerizable material for a sufficient length of time (say, thirty seconds) to effect cure of the polymer. During this time the shield covers, by contact, substantially all of the adjacent or surrounding surfaces of the teeth and any related structures. No light escapes from the end of the tip 9 except onto the material for curing.

Not only is the intense light confined to the selected area and prevented from escaping to cause difficulty elsewhere, but also the relatively soft shield 19 is effective to preclude any inadvertent touching of the hard or rigid tip 9 or of the sleeve 17 against the subjacent structures.

After use of the device on one patient, the collar 13 can readily be removed with its shield material and can easily and inexpensively be replaced by a similar, new structure. We claim:

1. A light shield for a dental handpiece having a tubular end terminating in a squared-off tip and having means for conducting light through said handpiece and to said end to discharge therefrom, comprising an annular shield collar having an inner cylindrical wall adapted to slip over said handpiece end, an annular end flange on said inner cylindrical wall adapted to abut said tubular end and defining a central opening in line with said light conducting means, an outer cylindrical wall connected to said inner cylindrical wall flange to define an annular space between said cylindrical walls, and an annular shield of spongy opaque material mounted in said annular space, said annular shield having a disc portion extending radially and axially beyond said tubular end and having a central opening therethrough in position to conduct said light coming fom said tubular end through the center of said annular shield.

* * * * *